United States Patent [19]
Bonnacker et al.

[11] Patent Number: 5,977,127
[45] Date of Patent: Nov. 2, 1999

[54] CILANSETRON PHARMACEUTICAL PREPARATION STABILIZED AGAINST RACEMIZATION

[75] Inventors: Ingo Bonnacker, Nordstemmen; Hartmut Koehn, Celle; Gerhard Kristen, Burgdorf; Christine Reichel, Wedemark, all of Germany

[73] Assignee: Solvay Pharmaceuticals GmbH, Hannover, Germany

[21] Appl. No.: 09/126,751

[22] Filed: Jul. 31, 1998

[30]     Foreign Application Priority Data

Aug. 1, 1997 [DE] Germany ............................ 197 33 271
Mar. 27, 1998 [DE] Germany ............................ 198 13 661

[51] Int. Cl.$^6$ ............................ A01N 43/42; A61K 31/44
[52] U.S. Cl. ........................ 514/284; 514/397; 514/962; 514/960; 514/970; 514/973; 424/451; 424/452; 424/464; 424/465; 424/489
[58] Field of Search ..................................... 514/284, 397, 514/962, 960, 970, 973; 424/451, 452, 464, 465, 489

[56]           References Cited

U.S. PATENT DOCUMENTS 4,939,136  7/1990  Haeck et al. ............................ 514/183
5,438,068  8/1995  Eeckhout et al. ....................... 514/397
5,663,343  9/1997  van der Meij et al. .................. 546/72

*Primary Examiner*—Frederick Krass
*Attorney, Agent, or Firm*—Evenson, McKeown, Edwards & Lenahan, P.L.L.C.

[57]           ABSTRACT

Solid and liquid pharmaceutical preparations containing cilansetron or its acid addition salts as active substance which include an amount sufficient to stabilize cilansetron against racemization, of a physiologically compatible water-soluble acid additive selected from monobasic or multibasic organic acids having 2 to 12 carbon atoms with a first $p_s$ value between 1.1 and 4.8, acid salts of the aforementioned multibasic organic acids, and acid salts of multibasic mineral acids having a first available $pK_s$ value between 1.5 and 7.5, as well as the use of such acid additives for stabilizing cilansetron against racemization in pharmaceutical preparations.

18 Claims, No Drawings

CILANSETRON PHARMACEUTICAL PREPARATION STABILIZED AGAINST RACEMIZATION

BACKGROUND OF THE INVENTION

The present invention relates to solid and liquid pharmaceutical preparations containing cilansetron as an active substance, and which further contain a sufficient quantity of physiologically compatible water-soluble acid additive to stabilize the cilansetron against racemization. The invention further relates to the use of these acid additives for the stabilizing of cilansetron against racemization in pharmaceutical preparations.

Cilansetron is the generic designation for R-(−)5,6,9,10-tetrahydro-10-[(2-methyl-imidazol-1-yl) methyl]-4H-pyrido [3.2.1-jk]carbazol-11(8H)-one, which is known from U.S. Pat. No. 4,939,136 (=EP 297,651). The compound can be produced in a known manner according to the methods indicated in this patent or analogous thereto. Furthermore, a method is known from U.S. Pat. No. 5,663,343 (=EP 768, 309) for obtaining pure enantiomers of cilansetron. Cilansetron has 5 HT-antagonistic properties and can be used as a pharmaceutically active substance. The use of cilansetron for treating diseases of the lower intestines is known from U.S. Pat. No. 5,438,068 (=EP 601,345).

Cilansetron is an optically active compound. In pharmaceutical preparations, cilansetron can partially racemize over time, in particular in open storage, through environmental influences, so that then in addition to cilansetron its optical isomer can also be present in the pharmaceutical preparations. However, for pharmaceutical preparations it is desirable that the active substance contained therein be present in a largely constant, uniform form.

SUMMARY OF THE INVENTION

It is the object of the present invention to make available cilansetron or a physiologically compatible acid addition salt thereof as liquid and solid pharmaceutical preparations containing active substance, in which cilansetron is stabilized against racemization.

The invention thus relates to pharmaceutical preparations containing cilansetron or its physiologically compatible acid addition salts as an active substance in conventional therapeutically effective quantities, wherein the pharmaceutical preparations additionally contain an amount sufficient to stabilize cilansetron against racemization, of at least one physiologically compatible water-soluble acid additive.

In addition, the invention relates to a method of using these acid additives for stabilizing cilansetron or its acid addition salts against racemization, in particular in pharmaceutical preparations.

In accordance with the invention, cilansetron and its physiologically compatible acid addition salts are stabilized against racemization. Suitable acid addition salts include the salts of cilansetron with inorganic acids, for example sulfuric acid or hydrohalic acids, in particular hydrochloric acid, or with physiologically compatible organic acids. Preferably, cilansetron hydrochloride is used as an acid addition salt, which is present in solid form, usually as the monohydrate.

The following physiologically compatible water-soluble acid additives are suitable for stabilizing cilansetron or its acid addition salts against racemization in solid or liquid pharmaceutical preparations: monobasic or multibasic organic acids having 2 to 12 carbon atoms and a first $pK_s$ value between 1.1 and 4.8, acid salts of the aforementioned multibasic organic acids, and acid salts of multibasic inorganic acids having a first available $pK_s$ value between 1.5 and 7.5, and also mixtures of these compounds. In solid pharmaceutical preparations, solid water-soluble acid additives are used. In liquid pharmaceutical preparations, solid or liquid water-soluble acid additives can be used.

As solid acid additives, for example malonic acid, mandelic acid, oxalic acid, lactic acid, lactobionic acid, fumaric acid, maleic acid, tartaric acid, citric acid, ascorbic acid or physiologically compatible acid salts of these acids can be used. Also acid salts of inorganic acids, for example acid salts of phosphoric acid or sulfuric acid, and mixtures of these compounds, preferably acid salts of phosphoric acid such as physiologically compatible dihydrogen phosphates, come into consideration. In liquid pharmaceutical preparations, in addition to the above-mentioned solid acid additives, physiologically compatible liquid organic acids, for example acetic acid, also can be used.

Suitable acid salts of multibasic acids include, for example, their physiologically compatible alkali- or alkaline earth metallic salts, in particular their sodium, potassium or calcium salts or their ammonium salts.

Pharmaceutical preparations of cilansetron in accordance with the invention contain cilansetron in usual pharmaceutically effective quantities. For example, solid pharmaceutical preparations may contain cilansetron in quantities between approximately 10 mg and approximately 250 mg per gram of preparation, whereas liquid preparations usually contain cilansetron in quantities of approximately 1 mg to approximately 10 mg per milliliter of preparation.

Preparations stabilized according to the invention preferably contain acid addition salts of cilansetron, in particular cilansetron hydrochloride. It has been found that the quantity of acids necessary for the formation of the acid addition salts of cilansetron alone is usually not sufficient to protect cilansetron effectively against racemization. As water-soluble acid components, the pharmaceutical preparations therefore contain the acids necessary for the formation of the acid addition salts of cilansetron and also additional acid additives. Satisfactory stabilization of cilansetron against racemization is reliably achieved only through formulating pharmaceutical preparations with a physiologically compatible water-soluble acid additive in accordance with the invention.

Insofar as organic acids with a first $pK_s$ value between 1.1 and 4.8 are used as acid additives in solid pharmaceutical preparations, the molar ratio of water-soluble acid components to cilansetron should be between approximately 1.02:1 and approximately 5.0:1, preferably between approximately 1.15:1 and approximately 3.0:1. Insofar as an acid addition salt of cilansetron is present, a corresponding portion of the acid content of the preparation is supplied by the acid content present in the acid addition salt. In solid pharmaceutical formulations of acid addition salts of cilansetron, therefore, the molar ratio of added water-soluble acid additives to cilansetron acid addition salt advantageously lies between approximately 0.02:1 and approximately 4.0:1, preferably between approximately 0.15:1 and approximately 2.0:1. Thus, for example, cilansetron in conventional 150 mg tablets containing 4.68 mg of cilansetron hydrochloride monohydrate, is effectively stabilized against racemization by a citric acid content of between approximately 0.05 mg and approximately 10.0 mg, preferably between approximately 0.3 mg and approximately 4.0 mg. The use of solid organic acids with a first $pK_s$ value between 1.1 and 4.8 in solid pharmaceutical preparations is preferred. In particular, ascorbic acid and/or citric acid can be used.

Insofar as in solid pharmaceutical preparations acid additives with a higher $pK_s$ value are used, for example between 4.8 and 7.5, the molar ratio of water-soluble acid components to cilansetron should advantageously amount to between approximately 4:1 and approximately 10:1, preferably between approximately 5:1 and approximately 8:1. Also the use of these weak acid additives in solid pharmaceutical preparations of cilansetron can cause a noticeable stabilizing of the active substance against racemization, in particular upon the ingress of moisture.

Insofar as solid pharmaceutical preparations contain acid addition salts of cilansetron, the higher the content of cilansetron acid addition salt in the preparation under consideration, the more stable against racemization the cilansetron in these preparations will be. As a function of the content of the cilansetron acid addition salt in the solid preparation, therefore, in the indicated range of quantities, higher or lower quantities of acid additives can be added. Thus, for example, in solid preparations with a higher cilansetron acid addition salt content, for example in 150 mg tablets containing 18.72 mg cilansetron hydrochloride monohydrate, a further stabilization of the active substance against racemization also can be achieved through the incorporation of an additional acid additive.

As a whole, the proportion of acid additives should not exceed 50% by weight of the solid preparations, in order to ensure good processability of the mixtures, for example a good capability of being compressed into tablets.

Preferred solid preparations according to the invention are those which produce aqueous solutions or suspensions having pH values between 2.5 and 4.5, preferably between 3.0 and 4.0, when dissolved in 2500 times the weight quantity of water, relative to the amount of cilansetron in the preparation. Thus, for example, pH values of 3.8 to 4.0 are produced if conventional 150 mg tablets having a cilansetron content of 4 mg and the compositions 1 to 4 according to the invention, indicated in Table 1, are decomposed in 10.0 ml water, and the pH value is determined in a known manner after complete dissolution of the water-soluble components. On the other hand, pH values of 5.0 to 5.3 are produced, if instead of the tablets 1 to 4 according to the invention, unstabilized comparison compositions, for example the tablets 1a to 4a in Table 1, are examined under identical conditions.

In order to stabilize cilansetron in solid pharmaceutical preparations against racemization, an overall content of water-soluble acid components of between approximately $5 \times 10^{-5}$ mole and approximately $2.5 \times 10^{-3}$ mole, preferably between $6 \times 10^{-5}$ mol and $8 \times 10^{-4}$ mole per gram of the solid preparations is usually sufficient. A higher content of acid additives is likewise possible, but generally does not provide any additional stabilizing effect.

Examples of solid pharmaceutical preparations include preparations to be administered orally such as tablets, coated tablets, capsules, powders or granules. Usually, solid pharmaceutical preparations according to the invention also contain conventional adjuvants and/or carrier substances, such as known fillers, binding agents, disintegrating agents, flow-regulating agents or separating agents.

Suitable fillers include sugars such as lactose, sugar exchange substances such as mannitol or xylitol, cellulose or cellulose derivatives such as microcrystalline cellulose, optionally modified starches such as optionally pregelatinized maize starch, or currently available inorganic fillers, for example bentonite.

Further adjuvants which can be used for example as binding agents, disintegrating agents, flow-regulating agents and/or separating agents, include cross-linked polymers of starch derivatives such as for example cross carmelose sodium or polyvinyl pyrrolidone derivatives such as cross-linked polyvinyl pyrrolidone, preferably cross-PVP, colloidal silicon dioxide or long-chain amphiphilic organic compounds such as stearic acid or glycerol fatty acid esters. Preferably, only substantially neutrally reacting adjuvants and/or carrier substances should be contained in solid preparations according to the invention.

According to the invention, cilansetron or its acid addition salt is contained in solid pharmaceutical preparations together with at least one physiologically compatible water-soluble acid additive and at least one of the adjuvants and/or carrier substances indicated above. The active substance can be mixed and formulated with the acid additive and the pharmaceutical adjuvants and/or carrier substances in a known manner. In order to produce solid medicament forms, the cilansetron can be mixed with the further components mentioned in a conventional manner and can be granulated wet or dry. Insofar as acid additives with a $pK_s$ value between 4.8 and 7.5 are used, it can be advantageous to granulate wet. The granules or powder can be poured directly into capsules or compressed into tablet cores in the usual manner. If desired, these can be coated to form pills or film-coated in a known manner.

In the production of solid preparations according to the invention, it is advantageous to initially granulate cilansetron or its acid addition salt with only a portion of the adjuvants and/or carrier substances, preferably with approximately 5–50% by weight of the quantity of adjuvants and/or carrier substances necessary as a whole for the production of a solid preparation, and with at least one acid additive as a pre-mixture in a known manner, and only then to add to this pre-mixture the further remaining adjuvants and/or carrier substances individually or as pre-mixed granules. Hereby, thorough mixing and direct contact of cilansetron with the acid additives in the solid preparations is achieved, whereby the stabilizing of cilansetron against racemization is influenced in a particularly favorable manner. Particularly advantageously, in this manner solid pharmaceutical preparations, in particular tablets, with a relatively low active substance content, for example tablets weighing 150 mg with a 2 mg cilansetron content, can be produced, or else solid preparations which contain as acid additives only those with a $pK_s$ value between 4.8 and 7.5.

Suitable liquid preparations according to the invention include aqueous solutions, suspensions or emulsions of cilansetron which can be filled in conventional liquid administration forms, for example ampoules. The active substance and acid components are naturally distributed homogeneously in these liquid preparations.

Usually, liquid pharmaceutical preparations are produced using an acid addition salt of cilansetron, preferably its hydrochloride. Insofar as cilansetron is used as base, a correspondingly higher quantity of acid additives is required in order to achieve stabilization of the active substance against racemization in accordance with the invention. The pH value of liquid preparations should be set at a desired value between pH 2.5 and 4.5, preferably between pH 3.0 and pH 4.0. In particular, known physiologically compatible buffer systems such as citrate buffers, phosphate buffers and/or acetate buffers, which are able to be adjusted in the range between pH 2.5 and pH 4.5, are suitable for this. Preferably a citrate buffer may be used.

In order to form a suitable buffer system, the physiologically compatible water-soluble acid additives can be used, preferably together with a quantity of a suitable base sufficient to form a physiologically compatible buffer system. Suitable bases include, for example, weak bases such as weakly basic salts of the organic acids which are able to be used according to the invention. A quantity of a stronger base such as an alkali metal hydroxide, for example sodium hydroxide, suitable for in situ formation of a basic salt or of a physiological buffer system, may also be used. Insofar as, accordance with the regulations of the "United States Pharmacopoeia" (=USP) and in all cases amounted to between 6.0 and 7.0. Usually, the measured pH value of the water which was used was 6.5.

The determinations of the (R)- or (S)- enantiomer contents of the active substance were carried out by High Performance Liquid Chromatography (=HPLC) on chiral column material (Chiradex, Merck company).

TABLE 1

| Example No. Components in weight proportions [mg] | Tablet | | | | | | | | | Granules | |
|---|---|---|---|---|---|---|---|---|---|---|---|
| | 1 | 2 | 3 | 4 | 5 | 6 | 1a | 2a | 3a | 4a | 7a |
| Cilansetron.HCl.H$_2$O | 4.68 | 4.68 | 4.68 | 4.68 | 4.68 | 4.68 | 4.68 | 4.68 | 4.68 | 4.68 | 4.68 |
| Pearlitol 300 DC ® | 80.52 | 80.52 | 0 | 0 | 80.82 | 78.52 | 81.52 | 81.52 | 0 | 0 | 225.32 |
| Maize starch | 0 | 0 | 0 | 0 | 49.5 | 0 | 0 | 0 | 0 | 0 | 130.0 |
| Starch 1500 | 53.6 | 0 | 0 | 53.6 | 0 | 46.6 | 53.6 | 0 | 0 | 53.6 | 0 |
| Avicel PH 200 ® | 0 | 53.6 | 53.6 | 0 | 0 | 0 | 0 | 53.6 | 53.6 | 0 | 0 |
| Lactose | 0 | 0 | 80.52 | 80.52 | 0 | 0 | 0 | 0 | 81.52 | 81.52 | 0 |
| Polyplasdone XL ® | 5.1 | 5.1 | 5.1 | 5.1 | 3.0 | 5.1 | 5.1 | 5.1 | 5.1 | 5.1 | 13.0 |
| Kollidon 25 ® | 0 | 0 | 0 | 0 | 4.9 | 0 | 0 | 0 | 0 | 0 | 13.5 |
| Aerosil 200 ® | 1.0 | 1.0 | 1.0 | 1.0 | 1.0 | 1.0 | 1.0 | 1.0 | 1.0 | 1.0 | 2.5 |
| Stearic acid | 4.1 | 4.1 | 4.1 | 4.1 | 4.1 | 4.1 | 4.1 | 4.1 | 4.1 | 4.1 | 11.0 |
| Citric acid | 0 | 0 | 0 | 0 | 2.0 | 0 | 0 | 0 | 0 | 0 | 0 |
| Ascorbic acid | 1.0 | 1.0 | 1.0 | 1.0 | 0 | 0 | 0 | 0 | 0 | 0 | 0 |
| NaH$_2$PO$_4$.2H$_2$O | 0 | 0 | 0 | 0 | 0 | 10.0 | 0 | 0 | 0 | 0 | 0 |
| Total [mg] | 150.0 | 150.0 | 150.0 | 150.0 | 150.0 | 150.0 | 150.0 | 150.0 | 150.0 | 150.0 | 400 | for example, citric acid is used as acid additive to a liquid pharmaceutical preparation, the formation of a physiologically compatible buffer system can be achieved through the addition of a suitable quantity of sodium hydroxide or through the addition of a suitable quantity of sodium citrate.

In the liquid preparations stabilized according to the invention, the overall content of acid additives and also the ratio of acid additives to cilansetron can vary over a relatively wide range. Thus, the acid additives can be contained in a quantity of approximately $2.5 \times 10^{-6}$ mole, to approximately $10.0 \times 10^{-5}$ mole, preferably from $7.5 \times 10^{-6}$ mole to $1.5 \times 10^{-5}$ mole per milliliter of the preparation. The ratio of acid additives to acid addition salt of the cilansetron can amount, for example, to between 0.15:1 and 8.0:1. Accordingly, the molar ratio of dissolved acid components to cilansetron in the liquid preparations then lies between 1.15:1 and 9.0:1. For physiological compatibility, liquid preparations in which the ratio of acid additives to acid addition salt of cilansetron amounts to between 0.3:1 and 2.0:1, may be preferred.

The liquid preparations may optionally contain conventional diluents such as water, oils, emulsifiers and/or suspension agents such as polyethylene glycols and the like. In addition, if desired, further adjuvants and/or additives can be added, such as for example preserving agents, taste correctors and the like. If desired, liquid preparations can be sterilized before or after filling. In the production of the liquid pharmaceutical preparations, it can be advantageous to work under protection from light.

The following examples are intended to explain the invention in further detail, without limiting its scope. In the examples, purified water according to the requirements of the Deutsches Arzneibuch (=DAB) (German Pharmacopoeia) was used. The pH value of the water used was determined before each experiment was carried out, in

EXAMPLES 1–4 AND 6 AND COMPARISON COMPOSITIONS 1a–4a

Production of tablets with and without acid component by direct tableting.

The tablet formulations 1 to 4, 1a to 4a and 6 indicated in Table 1 were produced by direct tableting. For this, the active substance or a pre-mixture containing the active substance and the acid additive, was mixed with the indicated adjuvants from the group mannitol (Pearlitol 300 DC®, by Roquette), fine-powdered lactose, maize starch, pregelatinized maize starch (Starch 1500®, by Colorcon) and/or microcrystalline cellulose (Avicel PH 201®, by FMC). Then highly dispersed silicon dioxide (Aerosil 200®, by Degussa), stearic acid and cross-linked polyvinyl pyrrolidone (Polyplasdone XL®, by GAF Chemicals) were admixed and the resulting mixtures were compressed on a rotary pelleting press into 150 mg tablets, so that each tablet contained 4 mg of the pure active substance.

EXAMPLES 5 AND 7a

Production of tablets and capsules with and without acid additive by granulation.

The tablet formulation 5 indicated in Table 1 and the granules 7a were produced by a granulation method. For this, the active substance was mixed with the mannitol and the maize starch in a mixer, and in the case of Example 5 the resulting mixture was thoroughly moistened with the citric acid, dissolved in the necessary quantity of a 20% solution of polyvinyl pyrrolidone (Kollidon 25™ from BASF) in demineralized water. If necessary, in both Examples 5 and 7a, demineralized water was added. The moist mixture was granulated in a high-speed mixer (Diosna), and the resulting raw granules were dried at 40° C. on trays and passed through a sieve. Then the highly dispersed silicon dioxide, the stearic acid and the polyvinyl pyrrolidone were admixed. The finished granules then, according to formulation, were either poured in portions of 400 mg by means of an automatic capsule machine into hard gelatine capsules of size 0, so that each capsule contained 4 mg of the pure active substance (granules 7a) or were compressed on a rotary pelleting press into tablets of 150 mg weight each, so that each tablet contained 4 mg cilansetron (tablet 5).

EXAMPLE 8
Production of liquid pharmaceutical preparations (ampoules) with acid additive.

A liquid preparation of cilansetron was produced with citrate buffer as acid additive of the composition:

| | |
|---|---|
| cilansetron.HCl.H$_2$O | 234 mg |
| citric acid monohydrate | 60 mg |
| NaCl | 900 mg |
| NaOH | 5 mg |
| demineralized water | 99.296 g |

The pH value of the solution amounted to approximately 3.6. For this, the active substance and the adjuvants were dissolved in the water under protection from light, wherein the solution was continuously gassed with nitrogen. The solution was then filtered through membrane filters having a pore width of 0.2 µm and filled by means of an automatic ampoule-filling installation in portions of 2 ml into 2 ml ampoules, so that each ampoule contained 4 mg of cilansetron base.

EXAMPLE 9
Comparison of the pH values in aqueous solutions or suspensions of various solid pharmaceutical preparations with and without acid additives.

The solid pharmaceutical formulations 1–6 according to the invention and also the comparison compositions 1a–4a and 7a not according to the invention, which are indicated above in Table 1, were added respectively into 10.0 ml water (pH=6.5) at room temperature. The formulation of Example 7a was added into 25.0 ml water under the same conditions. After decomposition of the preparations and complete dissolution of the water-soluble components, the pH values of the resulting aqueous solutions or suspensions were each measured with a glass electrode. The measured pH values are indicated in the following Table 2.

TABLE 2

| Solid pharmaceutical formulation No. | 1 | 2 | 3 | 4 | 5 | 6 | 1a | 2a | 3a | 4a | 7a |
|---|---|---|---|---|---|---|---|---|---|---|---|
| pH value | 4.0 | 4.0 | 3.9 | 3.9 | 3.3 | 4.8 | 5.3 | 5.0 | 5.2 | 5.1 | 5.2 |

A quantity of 4.68 mg of cilansetron hydrochloride monohydrate, corresponding to the active substance quantity of the above formulations, was dissolved in 10.0 ml water under the conditions indicated above. The pH value of the resulting solution was determined to be 5.45.

Stability Investigation I: Comparison of racemization rates of cilansetron in tablets with and without acid component.

The tablet formulations listed in Table 3 with (relates to tablets 1 to 4) and without (relates to tablets 1a to 4a) the addition of acid additive, were subjected to a storage test. After 4 weeks in each case the increase in the content of S-(+)-isomer of cilansetron resulting through racemization was determined in the individual formulations. The results of the storage tests are reported in Table 3.

TABLE 3

Increase in the content of S-(+)-isomer of cilansetron in tablets with acid additive and without acid additive after 4 weeks' storage.

| | | Increase of content of S-(+)-enantiomer in % Tablet | | | | | | | | |
|---|---|---|---|---|---|---|---|---|---|---|
| Storage condition | Relative humidity [%] | 1 | 2 | 3 | 4 | 6 | 1a | 2a | 3a | 4a |
| 30° C. closed | 60 | 0.10 | 0.10 | 0.10 | 0.20 | — | 0.20 | 0.20 | 0.20 | 0.30 |
| 30° C. open | 60 | 0.10 | 0.10 | 0.40 | 0.20 | — | 1.70 | 0.20 | 0.20 | 0.50 |
| 40° C. open | 75 | 0.40 | 0.40 | 0.40 | 0.40 | 0.10 | 1.70 | 0.70 | 0.70 | 1.70 |
| 50° C. closed | not determined | 1.60 | 1.10 | 1.60 | 1.70 | — | 0.70 | 3.50 | 2.30 | 2.20 |

As the measurement values indicated in Table 3 show, already after 4 weeks' storage, distinct differences can be established in the content of S-(+)-enantiomer resulting through racemization, in particular in the case of open storage, i.e. with the ingress of air and moisture and possibly increased temperature. In the formulations stabilized according to the invention, the increase here of the content of S-(+) enantiomer is significantly lower than in the non-stabilized comparison formulations.

Stability Investigation II: Racemization rate of cilansetron in liquid preparations with various pH values.

An aqueous, citrate-buffered stock solution of cilansetron was produced having the following composition:

| | |
|---|---|
| cilansetron.HCl.H$_2$O | 6.684 g |
| citric acid monohydrate | 30.2 g |
| NaCl | 9.0 g |
| NaOH | 11.5 g |
| 1N HCl | 1566.0 g |

From this stock solution, through the addition of the respectively necessary quantity of 1N HCl, sample solutions with pH values of 2.9; 3.3; 3.6; 3.8 and 4.0 were produced. The sample solutions were subjected to a storage test at two different temperatures (26° C. and 41° C.), and the content of S-(+)-enantiomer resulting through racemization of the active substance was determined after time intervals of 8 weeks (storage temperature 26° C.) or after 12 weeks and after 12 months (storage temperature 41° C.). The results of this storage test are listed in Table 4.

TABLE 4

Racemization rate of cilansetron in liquid preparations as a function of pH value and temperature.

| | Content of (+)-enantiomer in [%] at the time Storage temperature | | | |
|---|---|---|---|---|
| | | 26° C. | 41° C. | |
| pH value | t = 0 | 8 weeks | 12 weeks | 12 months |
| 2.9 | 1.25 | 2.72 | — | — |
| 3.3 | 1.26 | 2.20 | 1.50 | 3.63 |
| 3.6 | 1.21 | 1.66 | 1.41 | 3.55 |
| 3.8 | 1.21 | 1.92 | 1.29 | 3.19 |
| 4.0 | 1.13 | 1.76 | 1.44 | — |

It can be seen from the measured values indicated in Table 4 that in the investigated pH range cilansetron is most effectively protected against racemization between pH 3.6 and pH 4.0.

Stability Investigation III: Effect of pH value and temperature on racemization rate of cilansetron in liquid preparations.

Cilansetron hydrochloride monohydrate was dissolved in a concentration of 1% in 0.065 molar phosphate buffer. From this stock solution, through the addition of the necessary quantity of 1/15 molar aqueous sodium hydroxide solution, sample solutions were produced with pH values of 2, 3, 4, 5 and 6. The individual sample solutions were each stored at 61° C. for 1, 7, 14 and 28 days, and the rate constants of the racemization of cilansetron were determined in known manner assuming first order kinetics. The results of this test are listed in Table 5.

TABLE 5

Racemization rate constants of cilansetron in liquid preparations at different pH values and at 61° C.

| pH value | 2 | 3 | 4 | 5 | 6 |
|---|---|---|---|---|---|
| $k*10^{-3}$ [1/d] | 8.86 | 3.00 | 2.21 | 7.18 | 21.05 |

From the measurement values entered into Table 5 it can be seen that the racemization rate of cilansetron at pH values greater than pH 2 and less than pH 5, preferably between pH 3 and pH 4 is significantly less than at other pH values.

Stability Investigation IV: Storage stability of cilansetron in liquid preparations.

In the manner indicated in Example 8, a citrate-buffered liquid preparation of cilansetron with an active substance content of 2 mg/ml was produced and was filled into two different ampoule sizes of 2 ml and 4 ml. The pH value of the solutions amounted in each case to 3.7. The ampoules were subjected to a storage test. After 6 months and after 24 months in each case, the content of S-(+)-enantiomer in the ampoules was determined. The measurement values are listed in Table 6:

TABLE 6

Storage stability of cilansetron in stabilized liquid pharmaceutical formulations according to invention.

| | | | Content of (+)-enantiomer in [%] | | | |
|---|---|---|---|---|---|---|
| | | | | 6 months | 24 months | |
| Product | pH value | t = 0 | 40° C. | $k10^{-3}$[1/d] | 25° C. | $k10^{-5}$[1/d] |
| ampoules, 4 mg/2 ml | 3.7 | 1.6 | 4.0 | 1.37 | 3.7 | 3.0 |
| ampoules, 8 mg/4 ml | 3.7 | 1.5 | 3.8 | 1.31 | 3.9 | 3.4 |

From the calculated rate constants k it can be seen that with an average storage temperature of 25° C. the proportion of S-(+)-enantiomer in the quantity of active substance in the ampoules will not exceed 5% for approximately 3 years.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A solid pharmaceutical preparation comprising:
   a therapeutically effective amount of cilansetron or a physiologically acceptable acid addition salt thereof; and
   an amount of at least one physiologically compatible water-soluble acid additive sufficient to stabilize the cilansetron or cilansetron salt against racemization,
   wherein the water-soluble acid additive is selected from the group consisting of monobasic or multibasic organic acids having 2 to 12 carbon atoms and a first $pK_s$ value between 1.1 and 4.8, acid salts of the aforementioned multibasic organic acids, and acid salts of Physiologically compatible multibasic mineral acids having a first available $pK_s$ value between 1.5 and 7.5, and
   wherein the molar ratio of the water-soluble acid additive to the cilansetron or a physiologically acceptable acid addition salt thereof is from 1.02:1 to 10:1 and the water-soluble acid additive comprises at most 50% by weight of the preparation.

2. A liquid pharmaceutical preparation, comprising:
   a therapeutically effective amount of cilansetron or a physiologically acceptable acid addition salt thereof; and
   an amount of at least one physiologically compatible water-soluble acid additive sufficient to stabilize the cilansetron or cilansetron salt against racemization and to establish a pH in the liquid from 2.5 to 4.5,
   wherein the water-soluble acid additive is selected from the group consisting of monobasic or multibasic organic acids having 2 to 12 carbon atoms and a first $pK_s$ value between 1.1 and 4.8, acid salts of the aforementioned multibasic organic acids, and acid salts of physiologically compatible multibasic mineral acids having a first available $pK_s$ value between 1.5 and 7.5.

3. A liquid pharmaceutical preparation according to claim 2, wherein the acid additive comprises at least one physiologically compatible liquid organic acid.

4. A liquid pharmaceutical preparation according to claim 2, comprising a physiologically compatible buffer system set at a pH value in the range from 2.5 to 4.5.

5. A liquid pharmaceutical preparation according to claim 4, wherein said buffer system is selected from the group consisting of a citrate buffer, a phosphate buffer and an acetate buffer.

6. A liquid pharmaceutical preparation according to claim 2, comprising a molar ratio of acid additive to cilansetron in the range from 1.15:1 to 9.0:1.

7. A liquid pharmaceutical preparation according to claim 6, comprising from 0.3 to 2.0 mole of at least one acid compound selected from the group consisting of ascorbic acid, citric acid and physiologically compatible salts thereof per one mole of said physiologically acceptable salt comprising cilansetron hydrochloride.

8. A liquid pharmaceutical preparation according to claim 7, further comprising at least one pharmaceutical carrier or adjuvant.

9. A method of stabilizing cilansetron or a physiologically acceptable acid addition salt thereof against racemization in a pharmaceutical preparation, said method comprising incorporating in the preparation an effective cilansetron racemization stabilizing amount of at least one physiologically compatible water-soluble acid additive selected from the group consisting of organic monobasic or multibasic acids having 2 to 12 carbon atoms and a first $pK_s$ value between 1.1 and 4.8, acid salts of the foregoing multibasic acids, and acid salts of physiologically compatible multibasic mineral acids having a first available $pK_s$ value between 1.5 and 7.5, and wherein the molar ratio of the water-soluble acid additive to cilansetron or a physiologically acceptable acid addition salt thereof is from 1.02:1 to 10:1 and the water-soluble acid additive comprises at most 50% by weight of the preparation.

10. A method of preparing a solid pharmaceutical preparation containing a pharmaceutically effective amount of cilansetron or a physiologically compatible acid addition salt thereof, wherein the cilansetron is stabilized against racemization, said method comprising incorporating in said preparation an effective cilansetron racemization stabilizing amount of at least one physiologically compatible solid water-soluble acid additive selected from the group consisting of monobasic or multibasic organic acids having 2 to 12 carbon atoms and a first $pK_s$ value between 1.1 and 4.8, acid salts of the aforementioned multibasic organic acids, and acid salts of multibasic mineral acids having a first available $pK_s$ value between 1.5 and 7.5, wherein the molar ratio of the water-soluble acid additive to cilansetron or a physiologically acceptable acid addition salt thereof is from 1.02:1 to 10:1 and the water-soluble acid additive comprises at most 50% by weight of the preparation.

11. A method according to claim 10, comprising the steps of:

forming a premixture by mixing cilansetron or an acid addition salt thereof with the at least one acid additive and with from 5 to 50% by weight of a total quantity carrier or adjuvant substances in the solid pharmaceutical preparation, granulating the resulting premixture;

thereafter adding the remainder of the carrier or adjuvant substances to produce a final mixture; and forming the final mixture into a pharmaceutical dosage form.

12. A method according to claim 11, wherein the final mixture is formed into a pharmaceutical dosage form by pressing it into tablets or filling it into capsules.

13. A solid pharmaceutical preparation according to claim 1, wherein the acid additive comprises at least one substance selected from the group consisting of ascorbic acid, citric acid, fumaric acid, lactobionic acid, maleic acid, malonic acid, mandelic acid, lactic acid, oxalic acid, tartaric acid, acid salts thereof, and physiologically compatible dihydrogen phosphates and hydrogen sulfates.

14. A solid pharmaceutical preparation according to claim 1, comprising cilansetron hydrochloride.

15. A solid pharmaceutical preparation according to claim 1, wherein the acid additive comprises at least one solid monobasic or multibasic organic acid having 2 to 12 carbon atoms and a first $pK_s$ value between 1.1 and 4.8.

16. A solid pharmaceutical preparation according to claim 15, containing a molar ratio of water-soluble acid to cilansetron in the range from 1.02:1 to 5.0:1, and wherein the acid additive comprises at most 50% by weight of the preparation.

17. A solid pharmaceutical preparation according to claim 1, wherein an aqueous solution or suspension produced by dissolving or suspending the solid pharmaceutical preparation in an amount of water 2500 times the weight of cilansetron contained in the preparation, has a pH value in the range from 2.5 to 4.5.

18. A solid pharmaceutical preparation according to claim 17, comprising from 0.15 to 2.0 mole of said water-soluble acid additive comprising at least one of ascorbic acid or citric acid or mixtures thereof per one mole of said physiologically acceptable acid addition salt comprising cilansetron hydrochloride, and at least one pharmaceutical carrier or adjuvant.

* * * * *